(12) United States Patent
Cartier et al.

(10) Patent No.: US 8,783,089 B2
(45) Date of Patent: Jul. 22, 2014

(54) DEVICE AND METHOD FOR DETERMINING THE PROPERTIES OF AEROSOL FORMULATIONS

(75) Inventors: Regis Cartier, Wiesbaden (DE); Marc Egen, Ingelheim am Rhein (DE); Michael Krueger, Ingelheim am Rhein (DE); Cordula Krueger, legal representative, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 888 days.

(21) Appl. No.: 12/996,709

(22) PCT Filed: Jun. 8, 2009

(86) PCT No.: PCT/EP2009/057056
§ 371 (c)(1),
(2), (4) Date: Mar. 1, 2012

(87) PCT Pub. No.: WO2009/150134
PCT Pub. Date: Dec. 17, 2009

(65) Prior Publication Data
US 2012/0168634 A1    Jul. 5, 2012

(30) Foreign Application Priority Data

Jun. 9, 2008 (EP) .................................. 08104315

(51) Int. Cl.
*G01N 33/497* (2006.01)
*G01N 13/00* (2006.01)
*G01N 15/02* (2006.01)
*G01N 1/22* (2006.01)

(52) U.S. Cl.
CPC ........ *G01N 1/2208* (2013.01); *G01N 2013/006* (2013.01); *G01N 2015/0261* (2013.01); *G01N 2001/2223* (2013.01); *G01N 2001/2244* (2013.01)
USPC ......................................................... 73/23.3

(58) Field of Classification Search
USPC ......................................................... 73/23.3
See application file for complete search history.

(56) References Cited

U.S. PATENT DOCUMENTS 5,985,309 A * 11/1999 Edwards et al. .............. 424/426

OTHER PUBLICATIONS

International Search Report, Form PCT/ISA/210, for corresponding PCT/EP2009/057056; date of mailing: Aug. 4, 2009.
Riley et al, In Vitro Method for Determining the Dissolution Rate of Inhalation Aerosol, Respiratory Drug Delivery, May 15, 2008, pp. 541-544.
Salama et al, Preparation and Characterisation of controlled release co-spray dried drug-polymer microparticles for inhalation 2: Evaluation of in vitro release profiling methodologies for controlled release respiratory aerosols, European Journal of Pharmaceuticals and Biopharmaceuticals, Apr. 7, 2008, pp. 145-152, vol. 70.

(Continued)

*Primary Examiner* — Peter Macchiarolo
*Assistant Examiner* — Alex Devito
(74) *Attorney, Agent, or Firm* — Michael P. Morris; Alan R. Stempel

(57) ABSTRACT

A device (100) for determining the solution rate and release kinetics of aerosol formulations comprises an inhaler (2) connected to a cascade impactor (3), wherein a membrane (6) is disposed on a filter plate of the cascade impactor (2), and an air-liquid model system with a device for collecting measured data.

16 Claims, 3 Drawing Sheets

(56) References Cited

OTHER PUBLICATIONS

Figure 1:
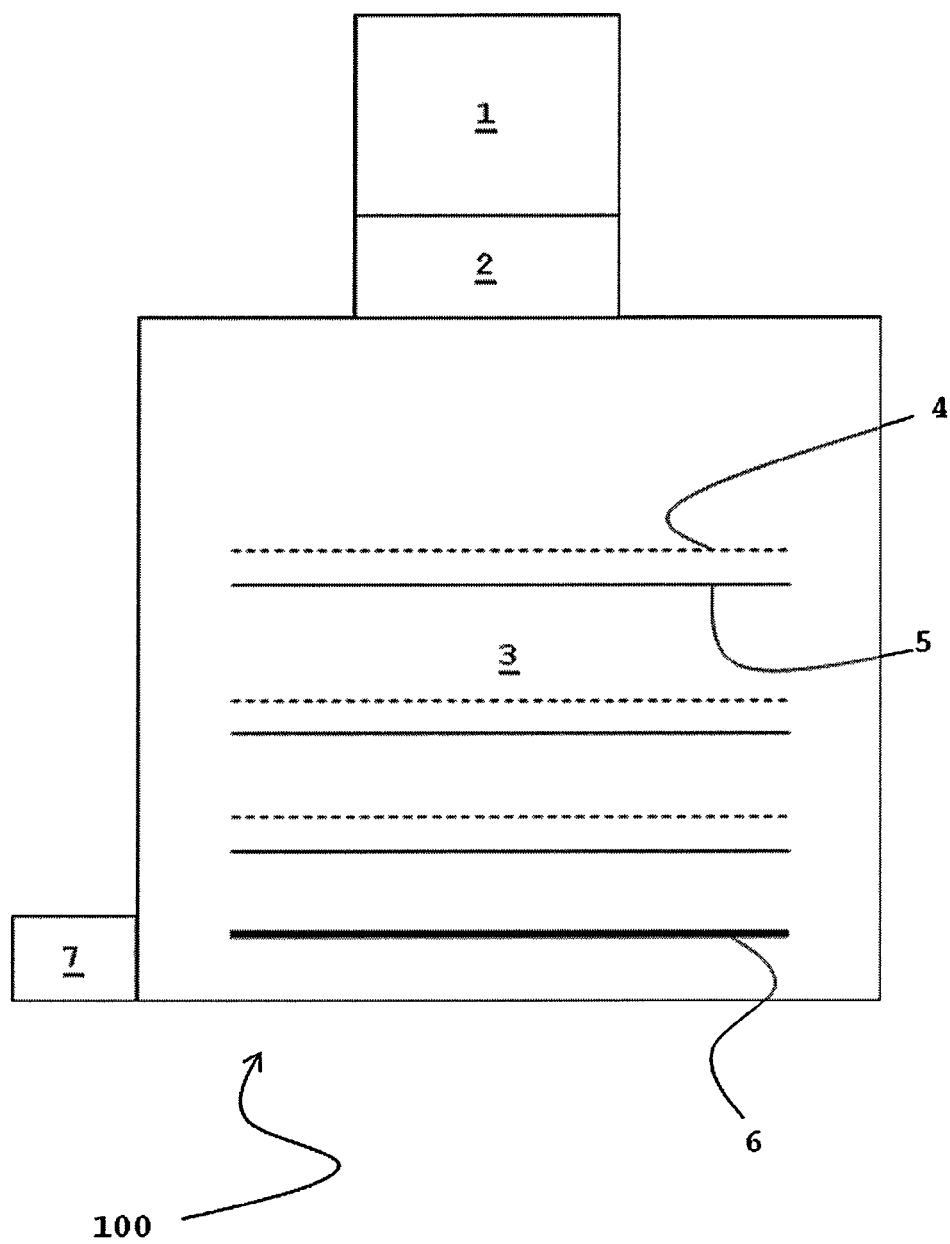

Davies et al, A Novel Method for Assessing Dissolution of Aerosol Inhaler Products, International Journal of Pharmaceuticals, Jan. 28, 2003, pp. 175-187, vol. 255.

Sivadas et al, A Comparative Study of a Range of Polymeric Microspheres as Potential Carriers for the Inhalation of Proteins, International Journal of Pharmaceuticals, Mar. 22, 2008, pp. 159-167, vol. 358, No. 1-2.

Cheng et al, Development of a Novel Nasal Nicotine Formulation Comprising an Optimal Pulsatile and Sustained Plasma Nicotine Profile for Smoking Cessation, Journal of Controlled Release, Feb. 19, 2002, pp. 243-254, vol. 79, No. 103.

El-Hameed et al, Preparation and in vitro Characterisation of Mucoadhesive Polymeric Microspheres as Intra-Nasal Delivery Systems, European Journal of Pharmaceuticals and Biopharmaceuticals, Jul. 27, 1997, pp. 53-60, vol. 44, No. 1.

McConville et al, Use of a Novel Modified TSI for the Evaluation of Controlled-Release Aerosol Formulations, Drug Development and Industrial Pharmacy, Jan. 1, 2000, pp. 1191-1198, vol. 26, No. 11.

\* cited by examiner

Fig. 3

DEVICE AND METHOD FOR DETERMINING THE PROPERTIES OF AEROSOL FORMULATIONS

The invention relates to a device for determining the solution rate and release kinetics of an aerosol formulation and a corresponding method therefor.

The following description relates to the testing of pharmaceutical formulations for inhalation in vitro. In particular it relates to the evaluation of the solution or release characteristics of medicaments which are deposited in the lungs after being inhaled. It also relates to the evaluation of formulations which persist as solids in the lung tissue for a significantly longer time than the dissolved form of the substances present. Hitherto, so called "dissolution tests" have been used for inhalants, which are operated either as a sealed system (beaker method, rotary basket method, blade stirrer apparatus) or as an open system (throughflow method). The release medium used is generally an aqueous solution which is intended to simulate the physiological environment of the target organ. The active substance is taken from the release device at defined times and determined analytically.

After inhalation the particles are deposited in different areas of the lungs depending on their aerodynamic properties. The main influencing variables are the particle size, the particle morphology and the particle porosity. For use by inhalation, particles measuring 1-5 μm, for example, are produced for depositing in the alveolar region.

Non-water-soluble solid formulations aggregate within minutes in the release medium, depending on their concentration, to form larger structures (~100 μm to a few mm), which in certain circumstances contain additional air inclusions. These form additional diffusion barriers and thereby influence the solution or release characteristics of the formulation. A dramatic apparent slowing down of release is the consequence. The present systems do not make it possible to make any pronouncement as to the actual release characteristics of poorly soluble particles for inhalation.

Moreover, most particle manufacturing methods result in particle mixtures with a relatively broad size distribution. Only the so called fine content of the mixture is deposited in the lungs during inhalation, while a considerable proportion (about 30-70%) of the mixture impacts in the pharynx and is therapeutically ineffective for topical application to the lungs. As the release characteristics are also influenced by the particle size, the therapeutically inactive fraction leads to an apparent delay in the in vitro release of the active substance. The systems currently used do not allow the fine content to be separated from the total population of the particles, which means that it is difficult to give any information as to the fine content.

To summarise, there are currently no standardised test systems which make it possible to investigate the release characteristics of inhalants in which the fine content is taken into consideration and in which the particles in dispersed form are brought into contact with the release medium.

Furthermore, determining the active substance content generally requires laborious analysis, often using high performance liquid chromatography (HPLC).

Moreover, the particles are submerged in the release medium. In the lungs, however, the particles rest on an interface between the lung fluid and the gaseous phase (air-liquid interface). Recently published results show that the release characteristics of solid formulations in the air-interface model behave differently than in the liquid-liquid-interface system.

The following studies recently published as contributions to conferences (posters) show proposed solutions to the disadvantages described above:

T. Riley et al., Respiratory Drug Delivery, 2008: A filter membrane was fixed to a stage plate of an NGI (New Generation Impactor). A dry powder formulation was then expelled through an MDI (metered dose inhaler) into the NGI. The stage plate and the air flow conditions were selected so that the result was deposition of 4.46 μm particles on the membrane. The membrane was then placed in a dissolution cell and simulated lung fluid was passed through it by the throughflow method. The active substance released was then determined using a sampler and analytical equipment provided downstream. This set-up makes it possible to investigate the fine content, provided that the placing of the membrane on the stage plate does not interfere with the operation of the NGI. A disadvantage of this is that the apparatus can only be operated in throughflow mode.

Y. J. Son et al., Respiratory Drug Delivery, 2008: this set-up also comprises the use of the NGI. In this case the filter membrane was placed in a container after the deposition test and used to measure the release of the active substance in a sealed dissolution test as described above.

The aim of the invention is to provide an apparatus for determining the solution rate and release kinetics of aerosol formulations, by means of which a concentration of active substance can be measured continuously during the release process. In addition, a corresponding method should be provided.

According to the invention this aim is achieved with an apparatus corresponding to the features of claim 1 and a method having the features according to claim 9.

In the apparatus, first of all a preferably standard commercial inhaler is provided with which, in normal operation, a person can administer an active substance. It may be, for example, a portable inhaler of the kind known under the trade mark HandiHaler®. Using the inhaler a dry powder formulation is dispersed so as to obtain a dry powder aerosol of the kind used for administration in humans.

Another embodiment also encompasses the use of an inhaler for applications in animals, e.g. an inhaler of the Dry Powder Insufflator DP4® type made by the company Penn-century.

Also provided is a cascade impactor, for example of the kind made by Anderson Samplers, Atlanta, USA. In a cascade impactor, nozzle plates arranged one behind the other with reducing nozzle diameters and impact surfaces arranged between the nozzle plates are used to filter a gas current laden with dust. The reduction in cross section increases the velocity of the gas. Whereas fine particles follow the gas current at slow speeds, larger particles are deposited on the filter disc. Thus, individual fractions with different particle sizes are obtained. Finally, a membrane serves to trap the remaining particles that have not yet been deposited, the membrane being arranged in front of the filter plate, when viewed in the direction of flow. Thus, particles of a specific size from a total population of particles are received on a membrane, preferably the fine content of the total population, and are immobilised on the membrane. Theoretically, all the particles could be immobilised in dispersed form on the membrane.

Finally, using an air-liquid model system the membrane is brought into contact with a release medium and an active substance concentration is monitored continuously during the release process using a device for detecting measurement data. The particles immobilised on the membrane are not exposed to any other forces such as shear forces, mechanical forces and the like during the contact with the release medium and depending on the situation they rest on an air interface in vivo.

The advantage of the invention is that a particle fraction that would actually be delivered from an inhaler and deposited in the lungs of a person can be tested for its solution or release characteristics. The air-liquid model system simulates the deposition environment of the lungs and there is continuous detection of measurement data using the apparatus, so that the analytical effort involved in the testing process is significantly less than in the prior art. For example, pharmaceutical aerosol formulations can be tested at the research and development phase and during manufacture and toxicological tests on lung pressure can be carried out with particles from the environment.

Obviously, in principle, any desired particles or medicinally active substances or mixtures of substances may be investigated. Moreover, the delivery of the particles from an inhaler onto a membrane using a cascade impactor can be spatially separate from the actual investigation of the membrane using the air-liquid model or in a single joint apparatus with, for example, an automated transfer of the membrane from the cascade impactor into an air-liquid model.

The use of the cascade impactor does not interfere in a particle separation process within the various nozzles or stages, as a result of which the particles actually deposited on the membrane are not affected. The immobilisation of the particles on the membrane is maintained even during the release process into the release medium in the model system, as the particles are not subjected to any additional forces. Within the air-liquid model system the conditions are simulated to be the same as in a patient's lung, as the particles rest on a liquid-air interface. Thus the particles are not subjected to any changes other than those that take place during dissolution in the release medium. Finally, continuous measurement data acquisition is possible.

Preferably, the material used for the membrane is cellulose, particularly regenerated cellulose, and it is arranged on the filter plate of the cascade impactor instead of a filter which would normally be provided. This cellulose material ensures virtually total immobilisation of the particles filtered out.

Moreover, the cascade impactor is operated to correspond to human breathing, for example with an air flow of 39 liters per minute over a period of 6.15 s, in order to simulate, as closely as possible, the quantity of air breathed in during actual inhalation, with the active substances dispersed from the inhaler.

For this purpose, in an advantageous embodiment, the membrane is such that it allows an air flow of at least 20 liters per minute, particularly 30 liters per minute, more preferably 39 liters per minute. The membrane has a pore size which allows the trapping of particles preferably with a pore diameter of 0.45 µm. A membrane material of this kind can easily be wetted with an aqueous solution and is chemically inert in aqueous solutions and does not normally enter into any interactions with a formulation.

According to a further feature, a two-chamber system is used as the air-liquid model system, preferably a Franz diffusion cell. A lower compartment is filled with a release medium which can be freely selected and the membrane is placed on the surface of the medium, ensuring that no air is still trapped between the release medium and the membrane. The upper part of the cell closes off the system and forms an air compartment.

In this embodiment the lower compartment is connected to a pump by tubes that carry the medium to a device for measurement data acquisition, for example a UV detector or a fluorescence detector. An active substance can be quantitatively detected using detectors of this kind. It goes without saying that the entire apparatus is preferably electronically controlled.

Moreover, the air-liquid model system is preferably designed to be temperature-controlled in order to simulate the body temperature inside the lungs.

Finally, the release medium is mixed with a stirrer system such as a magnetic stirrer in order to distribute an active substance taken up in the release medium more evenly inside the chamber.

It will be understood that the features mentioned above and described hereinafter may be used not only in the particular combination specified but also in other combinations. The scope of the invention is defined purely by the claims.

Figure 2:
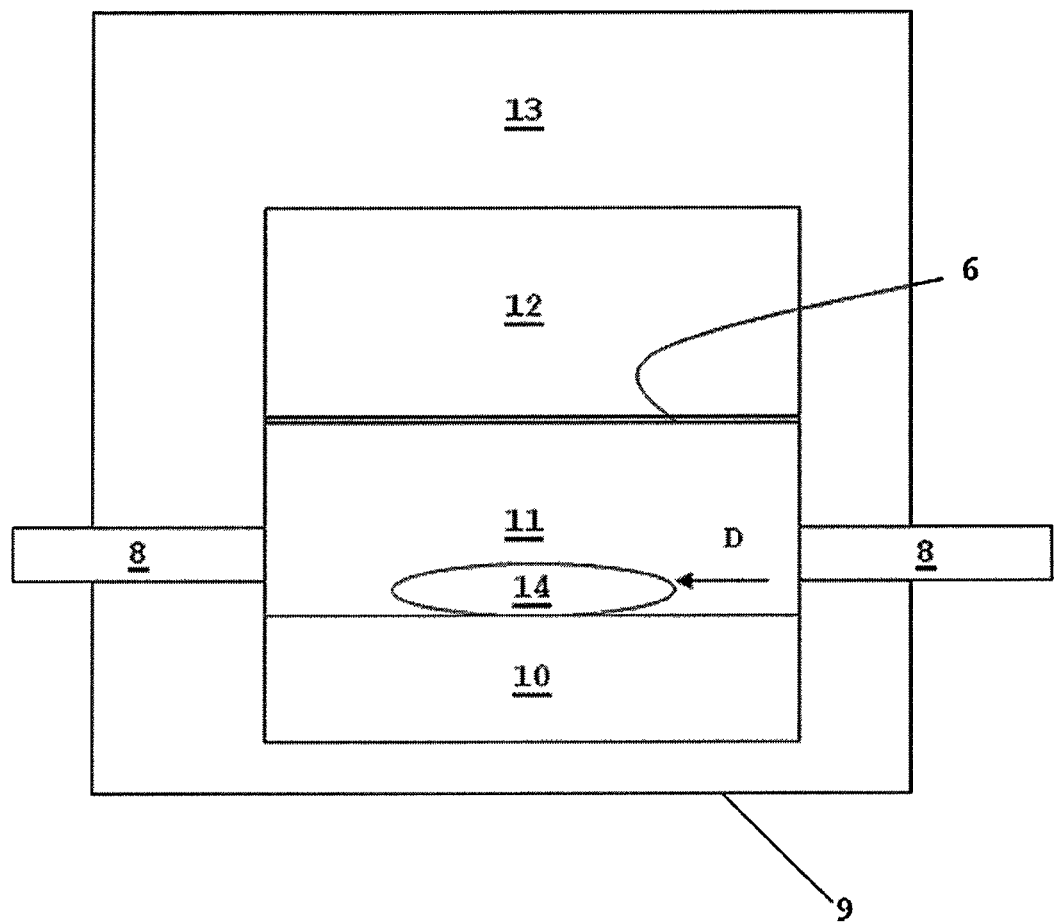

The invention is hereinafter explained in more detail by reference to an embodiment which refers to the associated drawings, wherein:

FIG. 1 shows an inhaler with a cascade impactor of the apparatus according to the invention, FIG. 2 shows a Franz cell of the apparatus according to FIG. 1, and FIG. 3 shows two measurement diagrams.

The apparatus 100 for determining the solution rate and release kinetics of aerosol formulations comprises an inhaler 1, which is commercially available under the trade mark HandiHaler, the mouthpiece of which is inserted in a corresponding socket or adaptor 2 of a cascade impactor 3. The various dotted lines 4 indicate the nozzles and the solid lines 5 indicate the nozzle plates of the successive stages of the cascade impactor 3. On the bottom stage of the cascade impactor 3, any particles that have not yet been filtered out are deposited or immobilised by means of a membrane 6, preferably consisting of regenerated cellulose. Of course, a corresponding vacuum is generated through a vacuum connection 7 in order to operate the cascade impactor 3 or inhaler 1 with, as far as possible, the same volume of breath as a person.

The membrane 6 is then arranged in a Franz diffusion cell 13 as shown in FIG. 2, which is part of the apparatus 100, while underneath the membrane 6 is disposed a first compartment 11 for receiving a liquid release medium free from air bubbles, which reacts continuously, as indicated by the connectors 8 and the throughflow arrow D, and a device for measurement data acquisition, such as a UV or fluorescence detector. Above the membrane 6 an air chamber is formed as the second compartment 12, and the entire diffusion cell 13 (Franz cell) is surrounded by thermal insulation 9 and can be temperature controlled in the desired manner by means of a hotplate 10. The release medium is mixed by means of a magnetic stirrer 14.

In order to characterise the system, first of all salbutamol sulphate, as the sample active substance, was added directly in the form of a dilute solution to the release medium (PBS, phosphate buffered saline) and measured at 225 nm in the photometer. The left hand diagram in FIG. 3 shows that after about four minutes' incubation the active substance concentration reaches a plateau. Salbutamol sulphate applied to the membrane 6 reaches the maximum concentration after about ten minutes. This means that the membrane 6 forms a diffusion barrier for about six minutes. The total system has a reaction time of about ten minutes, i.e. changes in concentration caused by the release of active substance are detected with a ten minute delay. On the timescale of a typical release test over 24 hours this delay can be disregarded.

Then, spray-dried delayed-release powder particles of salbutamol sulphate are dispersed as a test formulation on a membrane 6, without an additional cascade impactor stage, and the release of the active substance in the release system is investigated.

As can be seen from the right hand diagram in FIG. 3, in an investigation of a total fraction, a burst drug release of 50% was measured and delayed release was observed over 24 hours. By inserting suitable cascade impactor plates it was then possible to investigate particles <2 μm and <5.8 μm for controlled release, as illustrated in the right hand diagram. The result obtained is a significant size dependency in the release kinetics: the smaller particles release the active substance faster. As the method of particle manufacture with the spray dryer used excludes particles less than 1 μm by the use of the cyclone, the fraction <5.8 μm can be equated to the fine fraction of the population.

To summarise, the results show that this measuring set-up is suitable for online measurement over at least 24 hours, dispersed particles are immobilised on the membrane 6 and particle mixtures of different aerodynamic diameter can be distinguished.

For acquiring the measurement data, first of all the inhaler is connected by means of the adaptor 2 to the cascade impactor 3 and an aerosol to be investigated is immobilised on the membrane 6 in the cascade impactor 3. The membrane 6 is placed in the Franz diffusion cell 13 which is surrounded by the thermal insulation 9. The connectors 9 configured as inlets and outlets serve to deliver a release medium passing through them to the apparatus for measurement data acquisition, such as a UV detector.

The invention claimed is:

1. A test system for determining the solution rate and release kinetics of aerosol formulations, comprising:
   an inhaler (1), which is connected to a cascade impactor (3), while a hydrophilic membrane (6) is disposed on a filter plate of the cascade impactor (3) and is charged with particles,
   a Franz diffusion cell (13) into which the hydrophilic membrane (6) is disposed after being charged in the cascade impactor (3), wherein a first compartment (11) for receiving a liquid release medium is disposed underneath the hydrophilic membrane (6) and an air chamber is formed as a second compartment 12 above the hydrophilic membrane (6) within the Franz diffusion cell (13), and wherein the hydrophilic membrane (6) is in contact with a release medium, and
   a device for measurement data acquisition wherein medium from the first compartment is carried,
   wherein the hydrophilic membrane (6) comprises a material selected from among acrylic copolymer, polyethylene sulphone, polysulphone, cellulose, cellulose derivatives, cellulose esters and regenerated cellulose, and the hydrophilic membrane (6) has a maximum thickness of 100 μm.

2. The test system according to claim 1, wherein the membrane (6) is made of cellulose.

3. The test system according to claim 1, wherein the cascade impactor (3) is operated to correspond to human breathing.

4. The test system according to claim 1, wherein the membrane (6) has a permeability of one of: (i) at least 20 liters per minute, and (ii) 39 liters per minute, and has a pore size of 0.45 μm.

5. The test system according to claim 1, wherein the device for measurement data acquisition is one of: (i) a UV detector, and (ii) a fluorescence detector.

6. The test system according to claim 1, wherein the Franz diffusion cell (13) is temperature controlled.

7. The test system according to claim 1, wherein a magnetic stirrer (14) is associated with the Franz diffusion cell (13).

8. A process for determining the solution rate and release kinetics of aerosol formulations, comprising the steps of:
   releasing an aerosol that is to be measured from an inhaler (2) by means of a cascade impactor (3), wherein a membrane (6) is disposed on a filter plate in the cascade impactor (3), and
   measuring the particles immobilised on the membrane (6) by means of a Franz diffusion cell (13), wherein in the Franz diffusion cell (13) a first compartment 11 for receiving a liquid release medium is disposed underneath the membrane (6) and an air chamber is formed as a second compartment 12 above the membrane (6), and a device for measurement data acquisition,
   wherein the membrane (6) is made of a material selected from along acrylic copolymer, polyethylene sulphone, polysulphone, cellulose, cellulose derivatives, cellulose esters and regenerated cellulose, and the membrane having a maximum thickness of 100 μm.

9. The process according to claim 8, wherein a membrane (6) made of cellulose is used.

10. The process according to claim 8, wherein the cascade impactor (3) is operated to correspond to human breathing with an airflow of 39 liters per minute over a period of 6.15 seconds.

11. The process according to one of claim 8, wherein the membrane (6) is used with a minimum permeability of one of: (i) 20 liters per minute, and (ii) 30 liters per minute and with a pore size of 0.45 μm.

12. The process according to claim 8, wherein one of: (i) a UV detector and (ii) a fluorescence detector, is used as the device for measurement data acquisition.

13. The process according claim 8, wherein the Franz diffusion cell (13) is temperature controlled.

14. The process according to claim 8, wherein a magnetic stirrer (14), is used to mix the liquid release medium.

15. The process according to claim 8 wherein a pump is used to carry the medium from the lower compartment by tubes to the device for measurement data acquisition.

16. The test system according to claim 1 wherein the lower compartment is connected to a pump by tubes that carry the medium to the device for measurement data acquisition.

* * * * *